(12) United States Patent
Francke et al.

(10) Patent No.: US 6,970,533 B2
(45) Date of Patent: Nov. 29, 2005

(54) SCANNING-BASED DETECTION OF IONIZING RADIATION

(75) Inventors: Tom Francke, Sollentuna (SE); Christer Ullberg, Sollentuna (SE)

(73) Assignee: XCounter AB, Danderyd (SE)

( * ) Notice: Subject to any disclaimer, the term of this patent is extended or adjusted under 35 U.S.C. 154(b) by 187 days.

(21) Appl. No.: 10/411,100

(22) Filed: Apr. 11, 2003

(65) Prior Publication Data

US 2004/0174947 A1 Sep. 9, 2004

(30) Foreign Application Priority Data

Mar. 6, 2003 (SE) ............................................. 0300589

(51) Int. Cl.$^7$ ................................................. G21K 5/10
(52) U.S. Cl. ............................ 378/146; 378/62; 378/87
(58) Field of Search ................................. 378/19, 98, 8, 378/146, 62, 87, 22

(56) References Cited

U.S. PATENT DOCUMENTS

| | | | |
|---|---|---|---|
| 4,811,373 A | * | 3/1989 | Stein ............................ 378/54 |
| 4,817,123 A | * | 3/1989 | Sones et al. .................. 378/98 |
| 5,025,376 A | | 6/1991 | Bova et al. |
| 5,650,626 A | | 7/1997 | Trauernicht et al. |
| 5,812,191 A | * | 9/1998 | Orava et al. ................. 348/308 |
| 5,841,833 A | * | 11/1998 | Mazess et al. .............. 378/98.9 |
| 6,067,342 A | | 5/2000 | Gordon |
| 6,118,125 A | | 9/2000 | Carlson et al. |
| 6,337,482 B1 | | 1/2002 | Francke |
| 6,373,065 B1 | | 4/2002 | Francke et al. |
| 6,385,282 B1 | | 5/2002 | Francke et al. |
| 6,414,317 B1 | | 7/2002 | Francke et al. |
| 6,476,397 B1 | | 11/2002 | Francke |
| 6,477,223 B1 | | 11/2002 | Francke |

FOREIGN PATENT DOCUMENTS

EP 0046609 A1 3/1982

OTHER PUBLICATIONS

Search Report.

* cited by examiner

*Primary Examiner*—Edward J. Glick
*Assistant Examiner*—Thomas R. Artman
(74) *Attorney, Agent, or Firm*—Harness, Dickey & Pierce, P.L.C.

(57) ABSTRACT

A scanning-based radiation detector apparatus for recording an image of an object comprises a 1D detector unit exposed to a fan-shaped ionizing radiation beam, after having interacted with the object; a device for moving the 1D detector unit and the fan-shaped beam relative the object while repeatedly detecting to thereby create a 2D image of the object; and a control device for controlling the repeated detections. The one-dimensional detector unit has an ionizing radiation sensitive thickness, which is larger than the thickness of the fan-shaped beam when impinging on the one-dimensional detector unit. To obtain a short exposure time of each 1D image, but still a high spatial resolution in the 2D image, a 1D image of the fan-shaped beam is recorded every n'th length unit of the movement, where n is not lower than essentially half the thickness of the fan-shaped beam in that length unit, but lower than the ionizing radiation sensitive thickness of the 1D detector unit in that length unit.

10 Claims, 4 Drawing Sheets

$\sim 0.5 bt2 \leq ss < bt2$  if $bt2 < dt$
$\sim 0.5 dt \leq ss < dt$  if $bt2 > dt$

SCANNING-BASED DETECTION OF IONIZING RADIATION

FIELD OF THE INVENTION

The invention relates generally to apparatuses and methods for scanning-based detection of radiation.

BACKGROUND OF THE INVENTION AND RELATED ART

Various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. A one-dimensional image is typically recorded each time the line detector, and optionally the radiation source, has been moved a distance corresponding to the width of the radiation sensitive area of the line detector.

Such scanning-based detection is time consuming and may be impractical if large areas should be imaged. Movement of the object being examined may occur during scanning, which could severely reduce the image quality obtained. Thus, the scanning should be made as fast as possible. The exposure, however, has still to be selected such that the images possess high signal-to-noise ratio and high dynamic range.

Further, the spatial resolution is often an important parameter. In many examinations it is desirable to obtain a spatial resolution, which is better than 100 microns, e.g. as good as 50 microns. This put very high demands on the detector being used—both in terms of a narrow radiation sensitive area and in terms of small readout elements or pixels. Alternatively or additionally, very high requirements are put on the radiation source and any collimators employed in order to produce a very thin planar beam of ionizing radiation. For instance, it is extremely difficult—if at all possible—to produce a high quality planar X-ray beam of a thickness of 50 microns and a modest intensity.

SUMMARY OF THE INVENTION

A main object of the invention is therefore to provide a scanning-based ionizing radiation detecting apparatus and method, which provide for measurement of extremely high spatial resolution, but where the strong requirements on the detector and the radiation source are relaxed.

In this respect there is a particular object to provide such an apparatus and such a method, which are uncomplicated and can produce high-quality two-dimensional images with excellent, signal-to-noise ratio, dynamic range, and image contrast.

A further object of the invention is to provide such an apparatus and such a method, which enable a fast scanning across the object to be examined.

A yet further object of the invention is to provide such an apparatus and such a method, which are reliable, accurate, and inexpensive.

These objects, among others, are attained by apparatuses and methods as claimed in the appended claims.

The inventors have found that by providing a one-dimensional detector unit with an ionizing radiation sensitive thickness, which is larger than the thickness of a fan-shaped beam of ionizing radiation which is exposed to the detector unit; and by controlling the scanning by the one-dimensional detector unit to obtain a one-dimensional image of the fan-shaped beam of ionizing radiation at every n'th length unit of the scanning, where n is not lower than essentially half the thickness of the fan-shaped beam in that length unit, but lower than the thickness of the fan-shaped beam in the same length unit, a scanning-based detection is achieved with high spatial resolution in the two-dimensional image recorded without the provision of extremely thin radiation beams, or extremely narrow detectors.

The scanning step length n is preferably considerably lower than the thickness of the fan-shaped beam, and more preferably essentially half the thickness of the fan-shaped beam.

If the thickness of a fan-shaped beam is larger than the radiation sensitive thickness of the one-dimensional detector unit the scanning step length is set to a value smaller than the radiation sensitive thickness of the one-dimensional detector unit, but not smaller than essentially half the radiation sensitive thickness of the one-dimensional detector unit.

The one-dimensional detector unit is preferably, but not exclusively, a gaseous based parallel plate detector unit. Other detector units that may be used include diode arrays, scintillator based arrays, CCD arrays, TFT- and CMOS-based detectors, liquid detectors, and solid-state detectors, e.g. one-dimensional PIN-diode arrays with edge-on, near edge-on or perpendicular incidence of X-rays.

Further characteristics of the invention, and advantages thereof, will be evident from the detailed description of preferred embodiments of the present invention given hereinafter and the accompanying FIGS. 1–4, which are given by way of illustration only, and thus are not limitative of the present invention.

DESCRIPTION OF PREFERRED EMBODIMENTS

Figure 1:
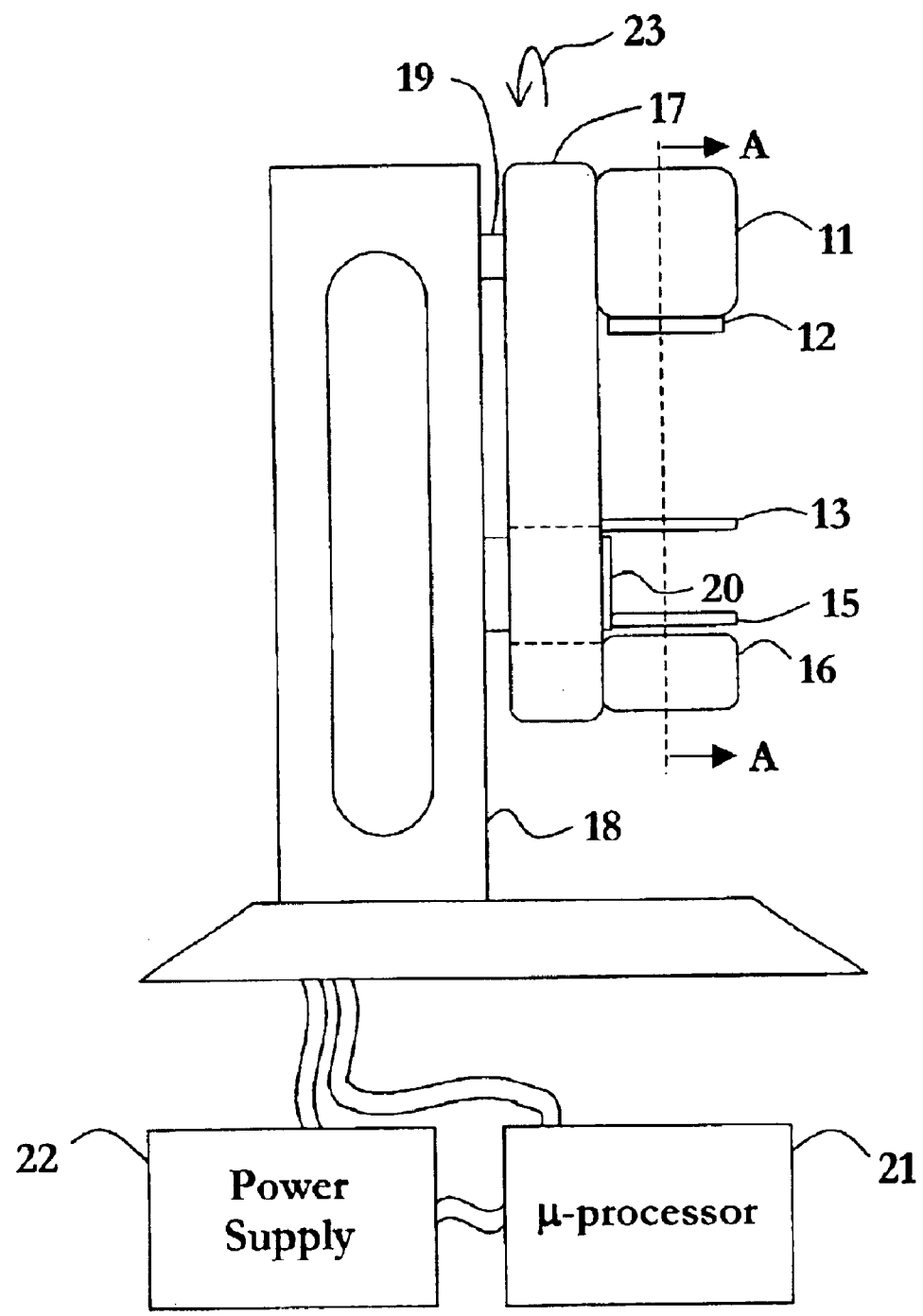
FIG. 1 illustrates schematically, in a side view, an apparatus for scanning-based X-ray imaging according to a preferred embodiment of the present invention.

From top to bottom the apparatus in FIG. 1 comprises an X-ray source 11, a filter device 12, a fan beam collimator 13, an object table or holder 15, and a one-dimensional detector unit 16.

The X-ray source 11 is a conventional X-ray tube having a cathode, which emits electrons, and an anode emitting X-rays in response to being struck by said electrons, said tube having an operating voltage, which is the voltage drop between said anode and said cathode, a tube current, which is the current between said anode and said cathode, and a focal spot size, which is the projected area in the direction of the emitted X-rays of said anode on which said electrons impinge.

A typical focal spot dimension is 0.1–1 mm. From such X-ray source it is difficult to produce a high quality planar radiation beam of a thickness of about 50 microns.

A filter device 12 is located just beneath the X-ray tube 11, which typically includes thin metallic foils acting as filters to absorb the lowest (and sometimes also the highest) energy photons, which do not contribute significantly to the image quality. The filter device may have variable spectral transmission characteristics.

The fan beam collimator 13 may be a thin foil of e.g. tungsten with a narrow radiation transparent slit etched away. The slit is aligned with a corresponding line-shaped sensitive area or entrance slit of the detector unit 16 that X-rays passing through the slit of the fan beam collimator 13 will reach the sensitive area or the detector unit 16. The width of the slit is indicated by bt1 in FIG. 2. Since the fan-shaped beam is divergent its thickness bt2 when reaching the detector unit 16 is bigger. For a distance from the X-ray tube 11 to the fan beam collimator 13 of about 45 cm, a distance from the X-ray tube 11 to the detector unit 16 of about 65 cm, a focal spot size of 300 $\mu$m and a collimator slit width bt1 of about 70 microns, the beam thickness bt2 at the detector unit 16 will be about 100 microns. The length of the slit is adapted so that the beam has a beam width of suitable size, e.g. 30–50 mm, when reaching the detector unit 16.

Figure 2:
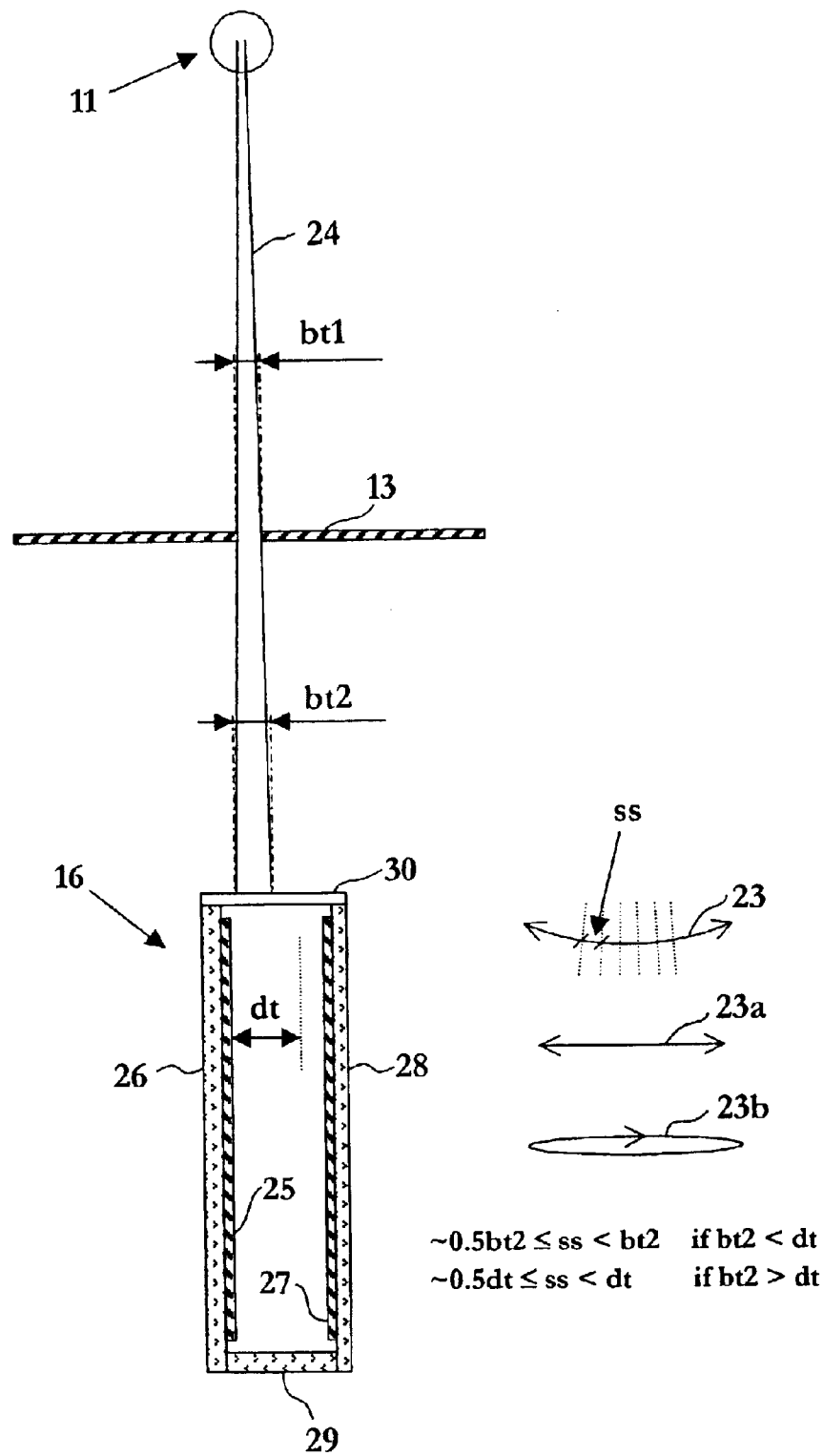
FIG. 2 is a schematic enlarged cross-sectional view of some of the components of the apparatus of FIG. 1 taken along the line A—A.

The detector unit 16 is illustrated more in detail in FIG. 2 and is oriented such that a planar or fan-shaped X-ray beam 24 can enter sideways between essentially planar cathode and anode arrangements. Each of the electrode arrangements includes an electrically conducting electrode layer 25, 27 supported by a respective dielectric substrate 26, 28, wherein the arrangements are oriented such that the conductive cathode 25 and anode 27 layers are facing each other. A radiation transparent window 30 is provided at the front of the detector unit to form an entrance for the fan-shaped beam 24 to the detector unit 16.

Preferably, the dielectric substrates 26, 28 and the window 30 define together with sidewalls 29 a gas-tight confinement capable of being filled with an ionizable gas or gas mixture. Alternatively, the electrode arrangements are arranged within an external gas-tight casing (not illustrated). The ionizable gas or gas mixture may e.g. comprise krypton and carbon dioxide or xenon and carbon dioxide.

The detector unit 16 comprises further a readout arrangement including a one-dimensional array of individual readout elements (not explicitly illustrated) for recording a one-dimensional image of the fan-shaped beam 24. Typically, the readout arrangement is integrated with the anode arrangement. The detector unit 16 may also comprise capabilities for electron avalanche amplification in order to record very low flux of X-rays, or detect each single X-ray with high efficiency.

When avalanche amplification is used, the one-dimensional detector unit 16 has an ionizing radiation sensitive thickness or height dt, i.e. a maximum thickness of a radiation beam which is contributing considerably to the signals detected by the detector unit 16, which is typically smaller than the distance between the conductive electrode layers 25, 27.

In one exemplary embodiment of the detector the distance between the electrodes is 200–2000 microns, the radiation sensitive thickness dt is 100–1500 microns, the depth (i.e. length in the direction of the radiation beam 24) of the detector is 10–100 mm, and the thickness (i.e. length perpendicular to the plane of FIG. 2) of the detector is 20–200 mm.

In an alternative version of the apparatus of FIG. 1, the detector unit is replaced by a detector arrangement comprising a plurality of one-dimensional detector units distributed in a one- or two-dimensional array. The fan beam collimator 13 is then replaced by a collimator with a plurality of narrow radiation transparent slits—one for each detector unit. The dimensions and orientations of the slits are such that each detector unit is exposed to a respective fan-shaped X-ray beam. By such version the scanning distance and time can be considerably shortened.

For further details regarding different kind of gaseous-based detector units for use in the present invention, reference is made to the following U.S. Patents by Tom Francke et al. and assigned to XCounter AB of Sweden, which patents are hereby incorporated by reference: U.S. Pat. Nos. 6,118,125; 6,373,065; 6,337,482; 6,385,282; 6,414,317; 6,476,397; and 6,477,223.

The X-ray tube 11, the fan beam collimator 13 and the detector unit 16 are attached to a common E-arm 17, which in turn is rotatably attached to a vertical stand 18 by means of a spindle 19 approximately at the height of the X-ray tube 11. In this manner, the X-ray tube 11, the fan beam collimator 13 and the detector unit 16 can be moved in a common pivoting movement relative to an examination object arranged on the object table 15 to scan the object and produce a two-dimensional image thereof. The pivoting movement is schematically indicated by arrow 23.

The object table 15 is firmly attached to a support 20, which in turn is firmly attached to the vertical stand 18. For this purpose the E-arm 17 is provided with a recess or similar in the E-arm 17 (illustrated by the dashed lines). During scanning, the object is kept still.

It shall be appreciated that the detector apparatus of FIG. 1 may be modified and arranged for linear movement of the X-ray tube 11, the fan beam collimator 13 and the detector unit 16 with respect to the object being examined. Such linear scanning movement is schematically indicated by arrow 23a in FIG. 2. Yet alternatively, the fan beam collimator 13 and the detector unit 16 may be rotated 16 in the horizontal plane with respect to the object being examined as being schematically indicated by arrow 23b in FIG. 2. Such rotational-based scanning is disclosed in U.S. Pat. Nos. 6,067,342 (Gordon) and 5,025,376 (Bova et al.), the contents of which being hereby incorporated by reference.

It shall further be appreciated that the apparatus of FIG. 1 may be modified such that the object is moved during scanning, while the X-ray tube 11, the fan beam collimator 13 and the detector unit 16 are kept at rest.

Furthermore, the detector apparatus comprises a microprocessor or computer 21 provided with suitable software for controlling the apparatus and readout and post-processing of the signals from the line detector unit 16 and a power supply 22 for supplying the detector unit and the microprocessor or computer 21 with power and for driving a step motor or similar housed in the vertical stand 18 for driving the spindle 19 and thus the E-arm 17.

In operation, X-rays are emitted from the X-ray tube 11 and pass through the filter device 12. Only x-rays passing through the slit of the fan beam collimator 13 traverse the object. In the object, the X-ray photons can be transmitted, absorbed or scattered. The X-rays that are transmitted leave the object and enter into the detector unit 16 and are detected. From the detection a one-dimensional image of the object is formed.

During scanning, the E-arm 17, holding the X-ray source 11, the fan beam collimator 13 and the detector unit 16, are moved in a pivoting movement such that the detector unit scans across the object in a direction, which is essentially parallel with the object table 15. At regular movement intervals, i.e. moved distances ss, the detected signals are read out and stored in a memory of the microprocessor 21. When the X-ray source and the scanning are stopped, a number of one-dimensional images of the object are formed and grouped together by the microprocessor 21 to create a two-dimensional image of the object.

In an alternative scanning technique the E-arm 17 is moved relative the object stepwise, and the one-dimensional detector unit 16 is detecting, while being still between the stepwise movements.

Each scanning step has the length ss as indicated at the arrow 23 in FIG. 2.

In the case as illustrated in FIG. 2 where the one-dimensional detector unit 16 has an ionizing radiation sensitive thickness dt, which is larger than the thickness bt2 of the fan-shaped beam 24 of ionizing radiation, the microprocessor 21 is adapted, according to the present invention, to control the detections by the one-dimensional detector unit 16 during the scanning to obtain a one-dimensional image of the fan-shaped beam 24 of ionizing radiation at every n'th length unit ss of the movement, where n is not lower than essentially half the thickness bt2 in that length unit, but lower than the thickness bt2 in the same length unit. In other words the scanning step ss can be defined as $$\sim 0.5 bt2 \leq ss < bt2 \quad (1)$$

provided that $$bt2 < dt \quad (2)$$

By such provisions a high spatial resolution in the two-dimensional image can be assured.

Preferably, the scanning step ss is considerably lower than the thickness bt2 of the fan-shaped beam 24 of ionizing radiation in the length unit to improve the spatial resolution in the two-dimensional image created from the number of one-dimensional images formed from the scanning. An optimum spatial resolution is obtained if the scanning step ss is essentially half the thickness bt2 of the fan-shaped beam 24 of ionizing radiation in the length unit.

Given a beam thickness bt2 of about 100 microns, the scanning step ss shall be lower, preferably considerably lower, than 100 microns, but not lower than about 50 microns. An optimum spatial resolution is obtained for a scanning step ss of 50 microns.

If, however, the one-dimensional detector unit 16 used has an ionizing radiation sensitive thickness dt, which is smaller than the thickness bt2 of the fan-shaped beam 24 of ionizing radiation (not illustrated), the microprocessor 21 is adapted, according to the present invention, to control the detections by the one-dimensional detector unit 16 during the scanning to obtain a one-dimensional image of the fan-shaped beam 24 of ionizing radiation at every i'th length unit ss of the movement, where i is not lower than essentially half the ionizing radiation sensitive thickness dt of the one-dimensional detector unit 16 in said length unit, but lower than the ionizing radiation sensitive thickness dt in the same length unit. In other words the scanning step ss can be defined as $$\sim 0.5 dt \leq ss < dt \quad (3)$$

provided that $$bt2 > dt \quad (4)$$

The scanning step is preferably considerably lower than the radiation sensitive thickness dt, and more preferably essentially about half the radiation sensitive thickness dt.

In a preferred version of the present invention the scanning step length ss is between about 0.5 and 0.8 times, preferably between about 0.5 and 0.7 times, more preferably between about 0.5 and 0.6 times, and most preferably approximately 0.5 times, the thickness bt2 or the thickness/height/width dt, whichever is smallest.

When the scanning step ss is reduced below the thickness bt2 or the thickness/height/width dt, whichever is smallest, the spatial resolution is improved gradually (to the cost of longer scanning times) until the scanning step ss is equal to the thickness bt2 or the thickness/height/width dt, whichever is smallest. If the scanning step is further reduced, no further improvement of the spatial resolution is obtained.

It shall further be appreciated that while the detector unit in the description above has been described as a gaseous-based ionization detector, wherein the freed electrons are drifted in a direction essentially perpendicular to the direction of the incident ionization, the present invention is not limited to such a detector. In fact, virtually any kind of detector can be used in the present invention as long as it is a one-dimensional detector capable of recording one-dimensional images of ionizing radiation, to which it is exposed. Examples of such detectors are scintillator-based detectors, PIN-diode arrays, TFT (thin film transistor) arrays, CCD (charged coupled device) arrays, CMOS circuits, or any other type of semiconductor devices.

Figure 3:
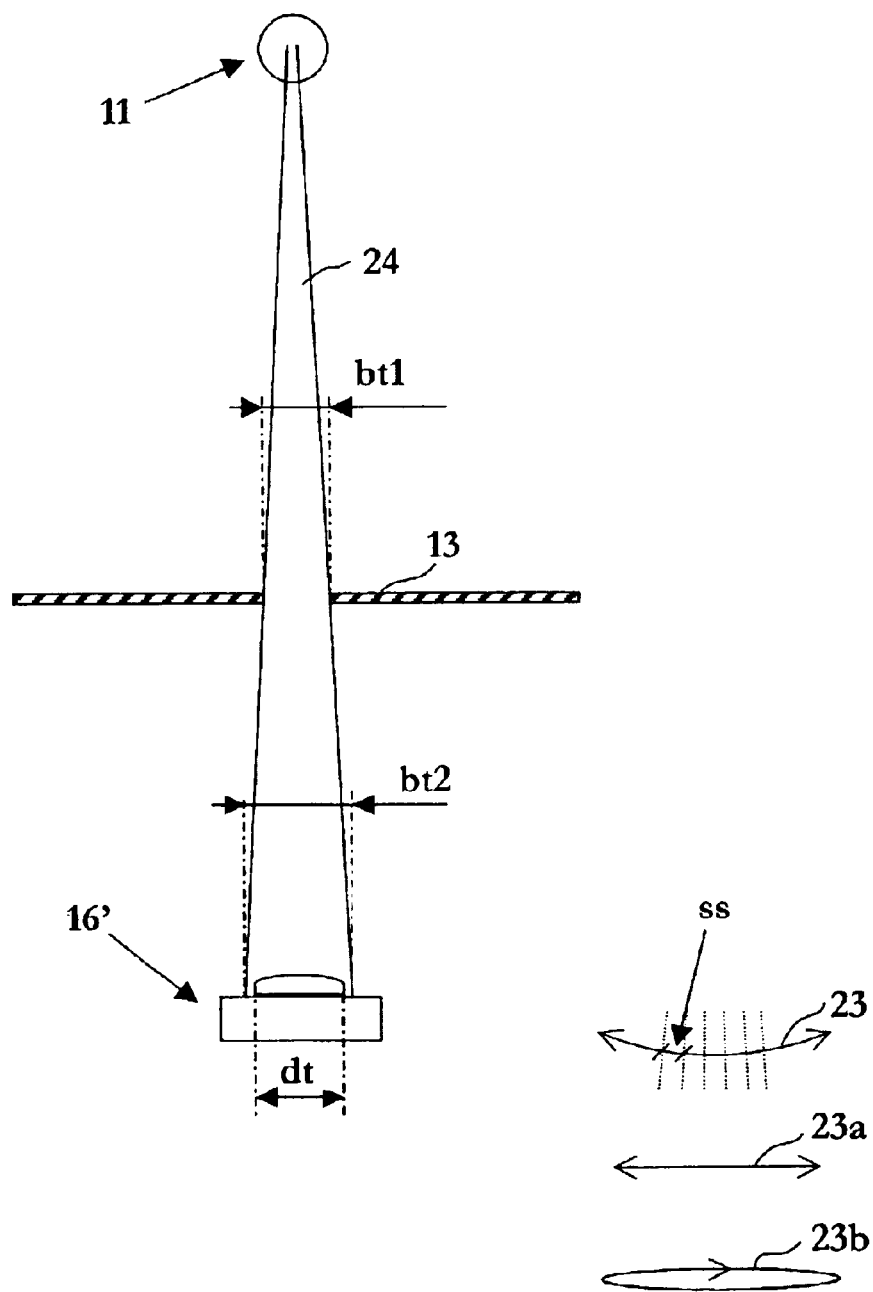
FIG. 3 is a schematic enlarged cross-sectional view of similar components of a detector apparatus according to another preferred embodiment of the invention.

FIG. 3 is a schematic enlarged cross-sectional view similar to the FIG. 2 cross-sectional view, but which illustrates a detector apparatus based on a linear semiconductor array 16'. The radiation sensitive thickness or width of the semiconductor array, i.e. dimension orthogonal to the extension of the array, is indicated by dt. Note that this Figure illustrates the case where the thickness bt2 of the planar radiation beam 24 at the entrance of the pin diode array is larger than the linear semiconductor array width dt.

Figure 4:
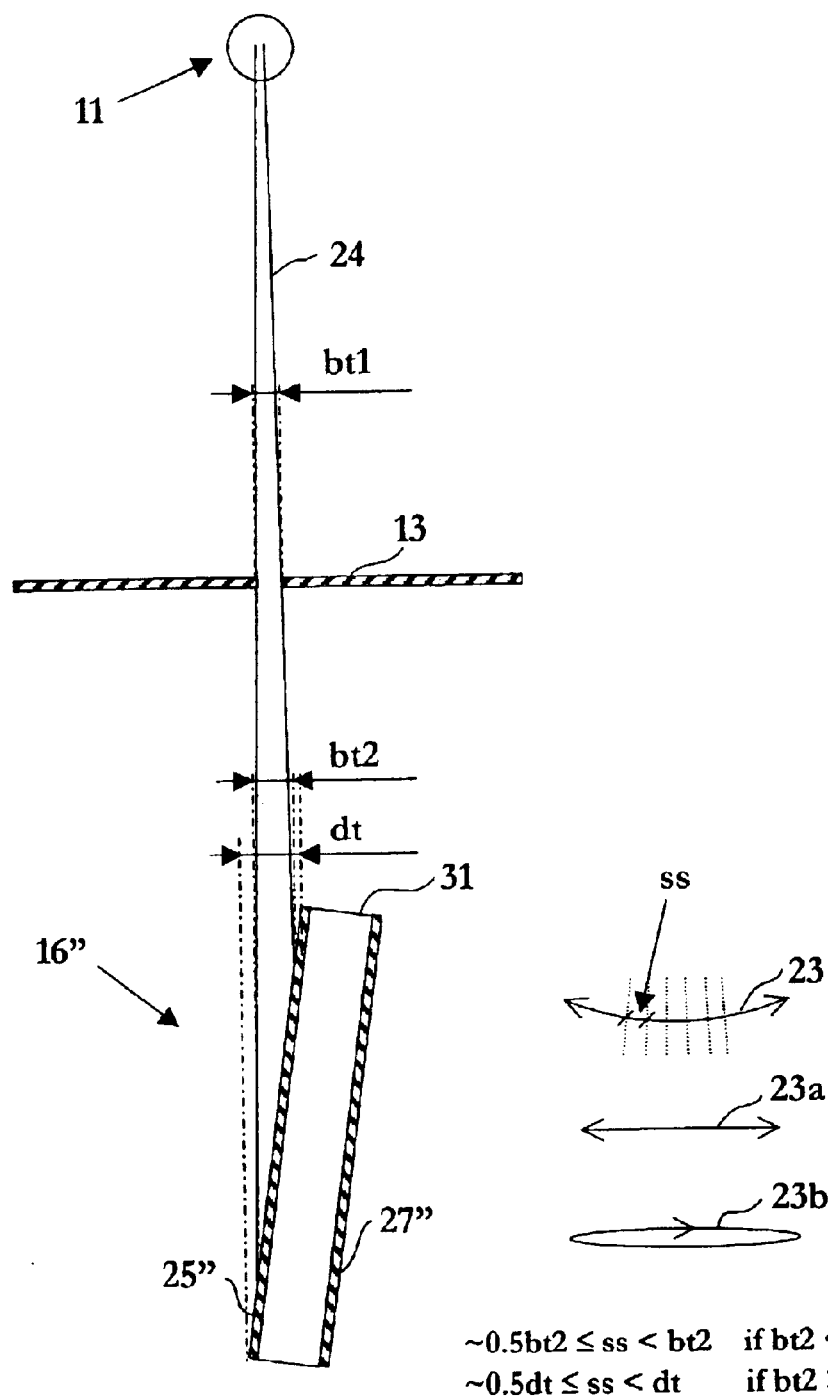
FIG. 4 is a schematic enlarged cross-sectional view of similar components of a detector apparatus according to yet another preferred embodiment of the invention.

FIG. 4 is a schematic enlarged cross-sectional view similar to the FIGS. 2–3 cross-sectional views, but which illustrates a detector apparatus based on a PIN-diode array 16". The detector comprises a plate 31 of doped silicon carrying a uniform metallic layer 25" on one surface and a metallic multiple strip layer 27" on an opposite surface. The detector apparatus is tilted with respect to the incident radiation beam so that the beam impinges onto the uniform metallic layer 25" of the detector apparatus at an acute angle. Within the silicon plate 31 the incident radiation interacts with the matter whereupon electrons and holes are created. By applying a suitable voltage over the metallic layers 25", 27" the electrons and holes are driven towards opposite surfaces of the silicon plate 31, and either ones of the electrons or holes are detected spatially resolved at the metallic multiple strip layer 27".

Note that FIG. 4 illustrates the case where the thickness bt2 of the planar radiation beam 24 at the entrance of the pin diode array is smaller than the active PIN-diode array width dt, which in turn depends on the depth of the PIN-diode array and the tilting angle.

Optionally, a further collimator is arranged in front of the detector (i.e. downstream of the object to be imaged), which may define the ionizing radiation sensitive thickness dt.

It shall yet further be appreciated that the present invention is equally applicable for recording two-dimensional images of radiation as scattered off an object instead of being transmitted there through.

What is claimed is:

1. A scanning-based radiation detector apparatus for recording a two-dimensional image of an object comprising:
   a one-dimensional detector unit exposed to a fan-shaped beam of ionizing radiation as transmitted through or scattered off said object, and arranged for repeated one-dimensional imaging of said fan-shaped beam of ionizing radiation, said fan-shaped beam of ionizing radiation having a thickness when impinging on said one-dimensional detector unit; and a device for moving said one-dimensional detector unit and said fan-shaped beam of ionizing radiation relative said object while said one-dimensional detector unit is arranged to repeatedly detect to thereby create a two-dimensional image of the object, wherein said one-dimensional detector unit has an ionizing radiation sensitive thickness, which is larger than the thickness of said fan-shaped beam of ionizing radiation; and said apparatus comprises a control device for controlling the repeated detections by said one-dimensional detector unit to obtain a one-dimensional image of said fan-shaped beam of ionizing radiation at every n'th length unit of the movement, where n is not lower than essentially half the thickness of said fan-shaped beam of ionizing radiation in said length unit, but lower than the thickness of said fan-shaped beam of ionizing radiation in said length unit.

2. The apparatus of claim 1 wherein n is considerably lower than the thickness of said fan-shaped beam of ionizing radiation in said length unit.

3. The apparatus of claim 1 wherein n is essentially half the thickness of said fan-shaped beam of ionizing radiation in said length unit.

4. The apparatus of claim 1 wherein said one-dimensional detector unit comprises an essentially planar cathode and anode, respectively, between which an ionizable gas is arranged, and a readout arrangement including a one-dimensional array of individual readout elements, the cathode and anode being oriented so that said fan-shaped beam of ionizing radiation enters said one-dimensional detector unit sideways between, and essentially parallel with, the cathode and the anode for ionizing the ionizable gas.

5. The apparatus of claim 4 wherein said one-dimensional detector unit comprises and electron avalanche amplifier.

6. The apparatus of claim 1 comprising a plurality of one-dimensional detector units, each exposed to a respective fan-shaped beam of ionizing radiation, as transmitted through or scattered off said object, and arranged for repeated one-dimensional imaging of the respective fan-shaped beam of ionizing radiation, to which it is exposed, wherein said plurality of one-dimensional detector units are distributed in a two-dimensional array on a common support;

said device for moving is adapted to move said plurality of one-dimensional detector units and said plurality of fan-shaped beams of ionizing radiation relative said object; and said device for controlling is adapted to control the repeated detections by said plurality of one-dimensional detector units to obtain a one-dimensional image from each of said plurality of one-dimensional detector units at every n'th length unit of said movement.

7. A scanning-based radiation detection method for recording a two-dimensional image of an object comprising the steps of:

exposing a one-dimensional detector unit to a fan-shaped beam of ionizing radiation, as transmitted through or scattered off said object, said fan-shaped beam of ionizing radiation having a thickness when impinging on said one-dimensional detector unit; and moving said one-dimensional detector unit and said fan-shaped beam of ionizing radiation relative said object while repeatedly detecting by said one-dimensional detector unit to thereby create a two-dimensional image of the object, wherein said one-dimensional detector unit has an ionizing radiation sensitive thickness, which is larger than the thickness of said fan-shaped beam of ionizing radiation; and the repeated detections are controlled by said one-dimensional detector unit to obtain a one-dimensional image of said fan-shaped beam of ionizing radiation at every n'th length unit of the movement, where n is not lower than essentially half the thickness of said fan-shaped beam of ionizing radiation in said length unit, but lower than the thickness of said fan-shaped bean of ionizing radiation in said length unit.

8. The method of claim 7 wherein n is considerably lower than the thickness of said fan-shaped beam of ionizing radiation in said length unit.

9. The method of claim 7 wherein n is essentially half the thickness of said fan-shaped beam of ionizing radiation in said length unit.

10. A radiation detector apparatus comprising a line detector, and a device for scanning said line detector across an object while being exposed to a fan-shaped ionizing radiation beam to thereby record a plurality of line images of said object, which may be put together to form a two-dimensional image of said object, wherein the scanned distance between two subsequent recordings of line images is between about 0.5 and 1 times the thickness of said fan-shaped beam when entering said line detector provided that the thickness of said fan-shaped beam when entering said line detector is smaller than or equal to the radiation sensitive thickness of said line detector; and the scanned distance between two subsequent recordings of line images is between about 0.5 and 1 times the radiation sensitive thickness of said line detector provided that the thickness of said fan-shaped beam when entering said line detector is smaller than or equal to the radiation sensitive thickness of said line detector.

* * * * *